United States Patent [19]

Amos

[11] Patent Number: 5,304,810
[45] Date of Patent: Apr. 19, 1994

[54] CONFOCAL SCANNING OPTICAL MICROSCOPE

[75] Inventor: William B. Amos, Cambridge, United Kingdom

[73] Assignee: Medical Research Council, London, United Kingdom

[21] Appl. No.: 972,462

[22] PCT Filed: Jul. 16, 1991

[86] PCT No.: PCT/GB91/01176
§ 371 Date: Feb. 16, 1993
§ 102(e) Date: Feb. 16, 1993

[87] PCT Pub. No.: WO92/01966
PCT Pub. Date: Feb. 6, 1992

[30] Foreign Application Priority Data
Jul. 18, 1990 [GB] United Kingdom ............... 9015793

[51] Int. Cl.$^5$ ............... G01N 21/00; G01N 21/63
[52] U.S. Cl. ............... 250/458.1; 250/349;
356/407; 356/417; 359/368; 359/372

[58] Field of Search ............... 250/339, 349, 458.1,
250/459.1, 461.1, 234, 341; 356/317, 318, 417,
407; 359/204, 368, 372, 373, 376, 378

[56] References Cited

U.S. PATENT DOCUMENTS

| | | | |
|---|---|---|---|
| 3,490,829 | 1/1970 | Weibrecht | 359/378 X |
| 4,417,789 | 11/1983 | Kano | 359/373 |
| 4,573,796 | 3/1986 | Martin et al. | 356/318 |
| 4,710,635 | 12/1987 | Chupp | 356/318 X |
| 4,796,964 | 1/1989 | Connell et al. | 359/204 |
| 5,065,008 | 11/1991 | Hakamata et al. | 250/234 X |
| 5,127,730 | 7/1992 | Brelje et al. | 356/318 |

*Primary Examiner*—Constantine Hannaher
*Assistant Examiner*—Edward J. Glick
*Attorney, Agent, or Firm*—Lee, Mann, Smith, McWilliams, Sweeney & Ohlson

[57] ABSTRACT

A confocal scanning optical microscope in which a specimen under test is simultaneously scanned with two distinct spots or slits of illumination and two output beams emitted from the specimen due to reflection or fluorescence are descanned and passed to separate stationary confocal apertures and detectors.

10 Claims, 2 Drawing Sheets

CONFOCAL SCANNING OPTICAL MICROSCOPE

BACKGROUND OF THE INVENTION

1. Field of the invention

This invention relates to an optical confocal scanning microscope.

2. Description of the Related Art

U.K. Patent Publication No. 2 184 321A discloses a confocal scanning optical microscope which is especially for the study of fluorescent or reflecting specimens. This instrument depends upon the focussing of light upon a single spot scanned over the specimen, which illuminated spot, after de-scanning, is imaged on a confocal aperture in front of a detector.

In the case where an image is to be formed of fluorescence from a specimen, the wavelength of the light directed on to the specimen is selected in such a way as to excite fluorescence. The emitted light is separated from the exciting light by a suitable beam splitter and is passed through wavelength-selective filters in such a way that the detector responds only to the light emitted by fluorescence. Instruments based on this design are commercially available. They contain a provision for subdividing the emitted light into beams of different wavelength ranges by a suitable beam splitter and filters. After this division, two dyes can be employed which emit different colours of fluorescence which can be distinguished at two detectors. Alternatively, a reflectance image can be obtained at the same time as a fluorescence image by the use of suitable beam-splitters, in accordance with accepted optical practice.

The prior art instruments work satisfactorily but all confocal scanning microscopes which rely on the use of a single scanning spot suffer from the defect that all the spectral selectivity of the system lies in the separation of the emitted or reflected beam into fractions of different wavelength. If there is considerable overlap between the fluorescent emission spectra of two dyes, they cannot be distinguished. For example, Bacallao et al comment in the Handbook of Confocal Microscopy, Plenum Press, 1990, that the commonly-used dyes fluorescein and rhodamine cannot be separated effectively in a system of this type. In order to achieve acceptable separation, it is necessary to vary the wavelength of excitation. This can be done by changing from one type of laser light to another, of spectrally different properties. First an image is obtained by operating the system with one type of excitation, and then a second image is obtained with a different type of exciting beam. This operation is slow and cumbersome.

Awamura, Ode and Yonezawa have described a microscope in which red, green and blue laser beams are scanned independently over the specimen, and the reflected beams are separated by dichroic filters and each executes a scanning motion over one of three separate linear CCD detector arrays. The description was published in the Proceedings of SPIE, The International Society for Optical Engineering (1987) Volume 765 pp 53-60. In principle, the system of Awamura et al might be used as a fluorescence microscope. It would then allow more than one type of dye to be excited in rapid succession during each line scan. However, in the case of two dyes with identical emission spectra, or a single ratiometric dye where the emission spectrum was to be monitored in a single waveband, the system of Awamura et al offers no advantage over that of White (U.K. Patent Application No. 2 184 321A), since neither system is capable of separating the two emission signals.

SUMMARY OF THE INVENTION

According to the present invention, there is provided a confocal scanning optical microscope comprising:

an optical scanning system;

means for simultaneously generating two or more input beams of optionally different spectral composition and of differing orientations such that after passage through the scanning system a specimen under test is scanned with two or more distinct and separate elemental areas of illumination; and two or more detectors respectively for receiving two or more output beams after de-scanning by the scanning means, each detector receiving an output beam substantially restricted to output light derived from one of the illuminated elemental areas.

The invention allows for two or more microscope channels having different excitation wavebands but identical emission wavebands, in order to make possible excitation ratio image measurements according to accepted practice.

The invention also allows for two or more microscope channels having identical excitation wavebands but different emission wavebands, in order to make possible emission ratio image measurements according to accepted practice.

The present invention is thus applicable to many kinds of scanning optical microscopes. It provides a means by which two or more spectrally distinct exciting spots or bars can be scanned together over the specimen during each sweep of the scanning system. The emission from each spot is passed individually and separately to a stationary confocal aperture leading to a detector, there being at least one aperture and detector for each spot.

The emitted beam from each spot, due to specimen fluorescence or reflection, may be filtered spectrally or subdivided between detectors in accordance with established practice, or may be passed unselectively to the detectors. It is thus possible to obtain, within a single scanning cycle, two or more complete images, each of which may differ in both excitation and emission waveband from the other images.

The invention may be considered as "a multiplexed optical system" because it involves two or more sets of independent but near-parallel beam paths passing through the same scanning system and objective lens, the optical paths being multiplexed in the literal sense of being folded together.

BRIEF DESCRIPTION OF THE DRAWINGS

Further features and advantages of the invention will be apparent from the following description of embodiments, making reference to the accompanying drawings, in which.

DESCRIPTION OF THE PREFERRED EMBODIMENTS

Figure 1:
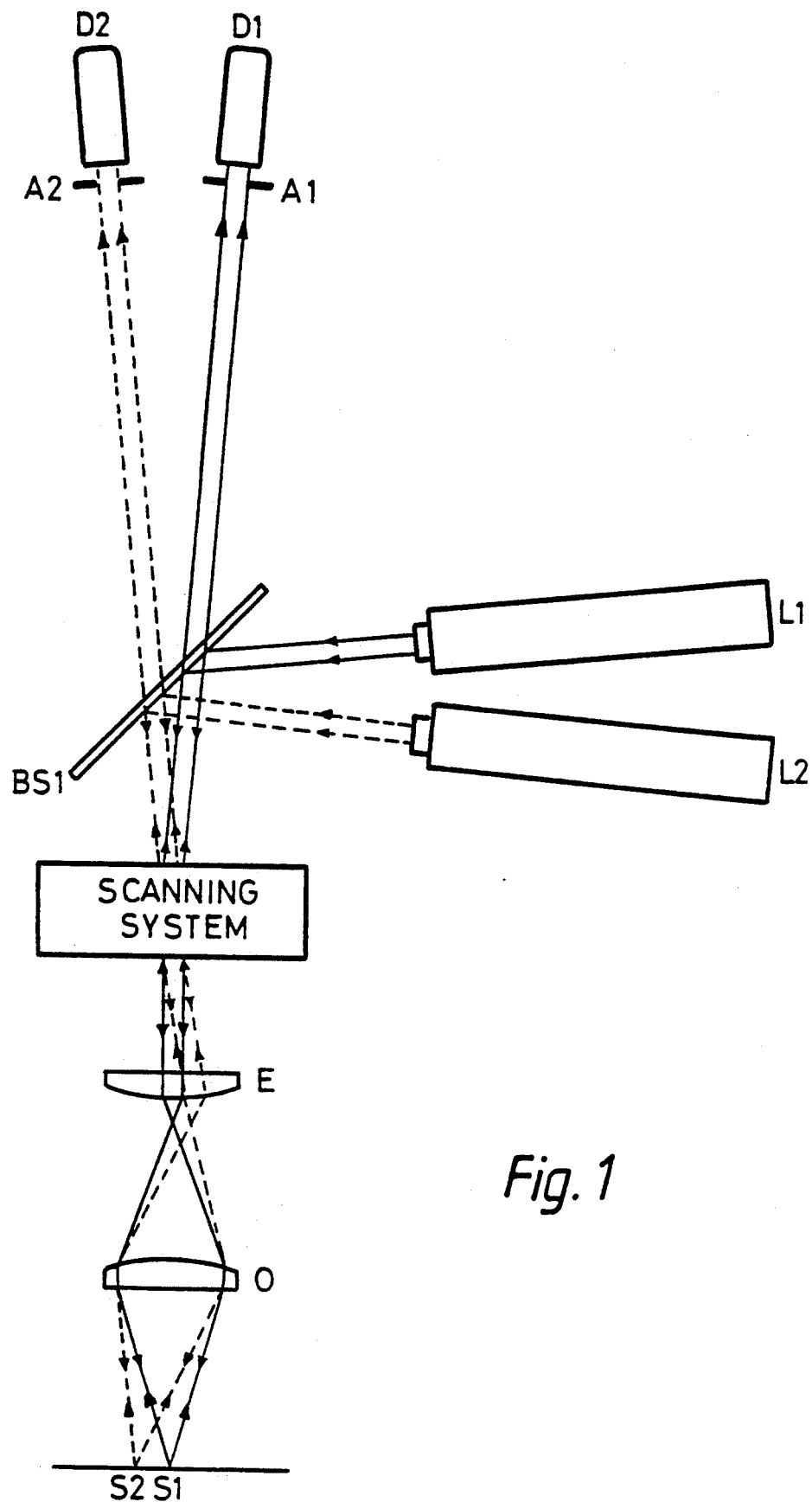
FIG. 1 is a schematic diagram of a confocal scanning microscope incorporating the multiplexed optical system of the present invention.

Referring to the drawings, the present invention provides an optical assembly which allows a number of independent optical channels to be used simultaneously for excitation in a laser confocal scanning microscope with an extended emission beam path, but is not restricted in application to this kind of microscope. The invention can be applied to confocal microscopes in which a bar or slit of light is scanned over the specimen as well as to those in which a single spot is scanned.

In FIG. 1, to simplify the diagram, only two independent light paths are shown, but there is no restriction on number in practice.

Light from two lasers, L1 and L2, with different spectral qualities, is directed on to a beam splitter BS1. The two beams are at a slight angle to each other, which angle is exaggerated in the diagram for the sake of clarity. The two beams are reflected into a scanning system as shown, which produces an angular scan of both beams simultaneously. The angular separation of the beams is maintained throughout the scan, and results, after passage through suitable microscope optics, typically an eyepiece E and an objective O, in the formation of two distinct moving spots of light S1 and S2 on the specimen.

Light is emitted from the specimen at S1 because of reflection or fluorescence and a portion of this emitted light passes back through the optical system, is descanned, i.e. reconverted into a stationary beam by the scanning system, passes through the beam splitter BS1 and falls on a confocal aperture A1 leading to a detector D1. Light from S2 passes through the optical system along a similar but distinct path and falls upon detector D2. The preferred angular separation is the smallest possible consistent with a satisfactory separation of the optical channels. To allow image registration, the small difference in time between the scanning of a given point in the specimen by the spots corresponding to S1 and S2 may be compensated by suitable conventional electronic means, for example by image processing software. It is not essential to the functioning of the system that the two or more spots should lie upon the same scan line.

Figure 2:
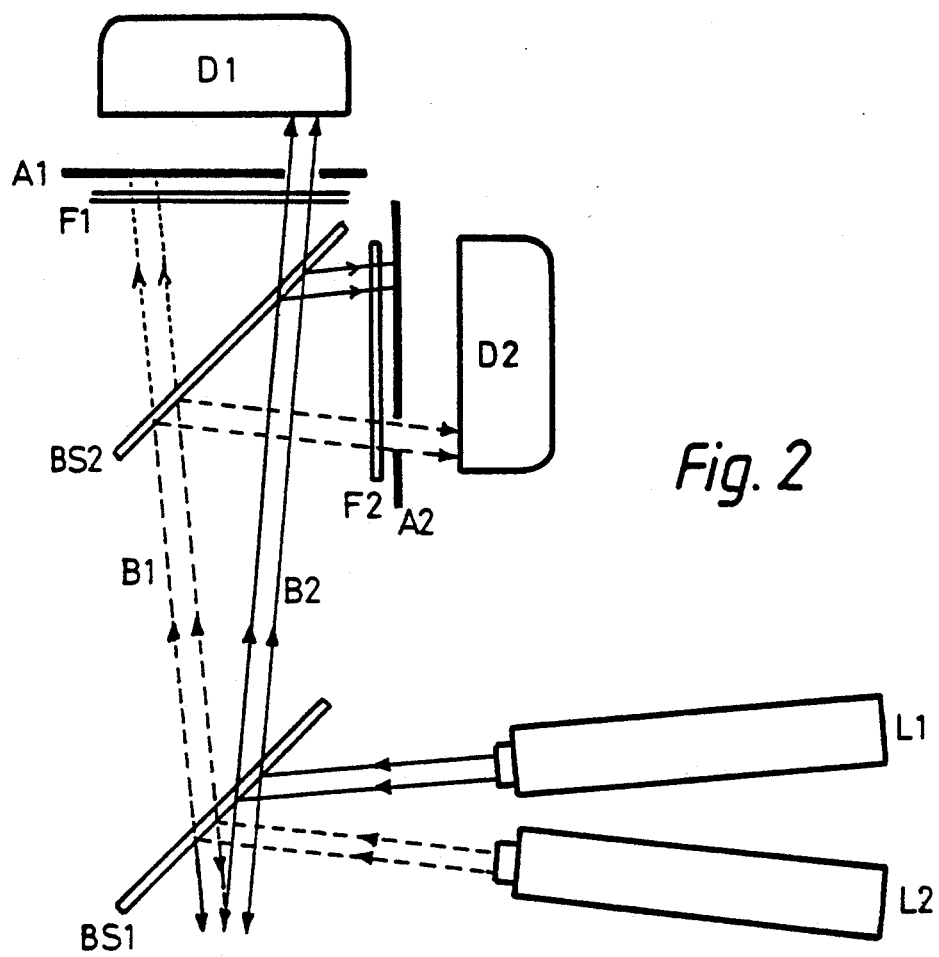
FIG. 2 is a schematic diagram showing an alternative and preferred optical arrangement for the upper part of FIG. 1.

In the preferred embodiment of FIG. 2, the scanning device and microscope are not shown in the figure, but should be taken to be the same as in FIG. 1. Beams from lasers L1 and L2 again pass at a small angle on to the beam splitter BS1. The returning beams, after passing through beam splitter BS1, pass to a second beam splitter BS2, which has dichromatic properties, so that most of the light in one of the beams, B2, passes through to confocal aperture A1 and thus to detector D1, while the other beam B1 is preferentially reflected to A2 and D2. This modification is preferred as it allows the use of the second beam splitter BS2 to achieve a selection of emission wavelengths, and also may be implemented by only slight modification of existing instruments. The separation of the emitted beams by wavelength may be improved by the addition of wavelength-selective filters F1 and F2.

The aiming of the emission beams, each on to the appropriate aperture A1 or A2, may conveniently be achieved by the use of mirrors (not shown) interposed between BS2 and the detectors D1 or D2.

Figure 3:
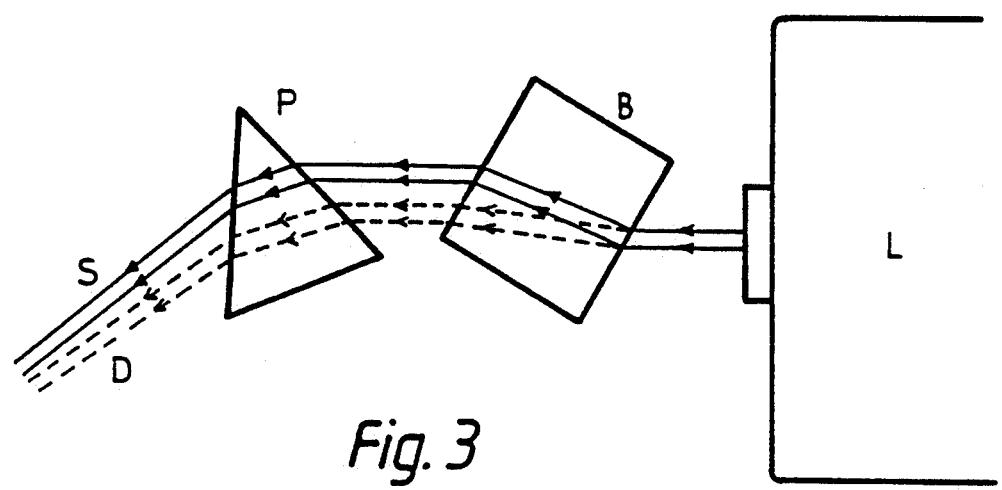
FIG. 3 is a schematic diagram showing an optical means by which several beams of different spectral properties may be obtained from a single (e.g. a multi-line) laser, for use in the present invention.

Additional mirrors and dichromatic reflectors may provide convenient means of achieving an appropriate angle between the input beams L1 and L2. For example, FIG. 3 illustrates one of many possible means by which light from a single multiline laser L may be separated into beams of different spectral composition and angle.

In this case, a parallel-sided block B of glass or other transparent material is used to produce a small lateral separation of the beams according to wavelength. The angle between the beams is then adjusted by passing them through a prism P, where they undergo different angular deviations because of the dispersing power of the prism. By appropriate orientation of the prism, parallel beams, each corresponding to a single wavelength, are generated, which converge towards the beam splitter BS1. The angle of convergence is determined by the angle of the prism and its refractive index and dispersive power. In the diagram, the solid line S indicates a beam at a shorter wavelength, which is more strongly refracted than the beam, shown by the dashed lines D, corresponding to light of a longer wavelength.

Various modifications of the above-described and illustrated arrangements are possible within the scope of the invention hereinbefore defined.

I claim:

1. A confocal scanning optical microscope comprising:
    an optical scanning system;
    means for simultaneously generating two or more input beams of optionally different spectral composition and of differing orientations such that after passage through the scanning system a specimen under test is scanned with two or more distinct and separate elemental areas of illumination; and
    two or more detectors respectively for receiving two or more output beams after de-scanning by the scanning means, each detector receiving an output beam substantially restricted to output light derived from one of the illuminated elemental areas.

2. A microscope according to claim 1, in which the input beams contain light for exciting the specimen respectively in differing wavebands and the output beams contain light emitted by the specimen in the same wavebands.

3. A microscope according to claim 1, in which the input beams contain light for exciting the specimen respectively in the same wavebands and the output beams contain light emitted by the specimen in different wavebands.

4. A microscope according to claim 1, in which the input beams contain light for exciting the specimen in respectively differing wavebands and the output beams contain light emitted by the specimen in different wavebands.

5. A microscope according to claim 1 including at least one stationary confocal aperture and detector for each elemental area, in which the output beam derived from the light emitted from each elemental area is passed individually and separately to a stationary confocal aperture leading to a detector.

6. A microscope according to claim 1, in which the elemental areas are in the form of spots or bars.

7. A microscope according to claim 1, in which the input beams are set at an angle to one another.

8. A microscope according to claim 1, in which a beam splitter provides for separation of output beams.

9. A microscope according to claim 1, in which one or more wavelength-selective filters enhance separation of the output beams by wavelength.

10. A microscope according to claim 1, including a multiline laser and a prism wherein distinct input beams are obtained by passing the light from the multiline laser through the prism.

* * * * *